(12) United States Patent
Neubardt

(10) Patent No.: US 9,585,678 B2
(45) Date of Patent: Mar. 7, 2017

(54) IMPLANTING FACET JOINT SCREWS PERCUTANEOUSLY

(76) Inventor: Seth L. Neubardt, Mamaroneck, NY (US)

( * ) Notice: Subject to any disclaimer, the term of this patent is extended or adjusted under 35 U.S.C. 154(b) by 444 days.

(21) Appl. No.: 13/253,953

(22) Filed: Oct. 5, 2011

(65) Prior Publication Data
US 2012/0083849 A1  Apr. 5, 2012

Related U.S. Application Data

(60) Provisional application No. 61/389,906, filed on Oct. 5, 2010.

(51) Int. Cl.
| | | |
|---|---|---|
| A61B 17/70 | (2006.01) | |
| A61B 17/17 | (2006.01) | |
| A61B 17/16 | (2006.01) | |
| A61B 17/84 | (2006.01) | |
| A61B 17/88 | (2006.01) | |
| A61B 17/86 | (2006.01) | |

(52) U.S. Cl.
CPC ...... *A61B 17/1757* (2013.01); *A61B 17/1671* (2013.01); *A61B 17/846* (2013.01); *A61B 17/8897* (2013.01); *A61B 90/06* (2016.02); *A61B 17/1697* (2013.01); *A61B 17/7064* (2013.01); *A61B 17/848* (2013.01); *A61B 17/864* (2013.01); *A61B 2090/067* (2016.02)

(58) Field of Classification Search
CPC .............. A61B 17/1757; A61B 17/864; A61B 17/8897; A61B 2019/467
USPC ................. 606/247, 304, 102, 104
See application file for complete search history.

(56) References Cited

U.S. PATENT DOCUMENTS

| | | | |
|---|---|---|---|
| 4,738,253 A | 4/1988 | Buechel et al. | |
| 4,907,577 A | 3/1990 | Wu | |
| 5,634,911 A * | 6/1997 | Hermann et al. | 604/256 |
| 6,113,601 A | 9/2000 | Tatar | |
| 6,547,795 B2 * | 4/2003 | Schneiderman | 606/96 |
| 7,060,068 B2 | 6/2006 | Tromanhauser et al. | |
| 7,235,076 B2 | 6/2007 | Pacheco | |
| 7,396,360 B2 | 7/2008 | Lieberman | |
| 7,717,919 B2 | 5/2010 | Assell et al. | |
| 7,740,635 B2 | 6/2010 | Lieberman | |
| 8,267,938 B2 * | 9/2012 | Murphy | 606/91 |
| 2003/0208202 A1 | 11/2003 | Falahee | |
| 2005/0154397 A1 * | 7/2005 | Ashby et al. | 606/96 |
| 2006/0064099 A1 * | 3/2006 | Pavlov et al. | 606/72 |

(Continued)

*Primary Examiner* — Eduardo C Robert
*Assistant Examiner* — Atiya Mahmud
(74) *Attorney, Agent, or Firm* — Law Office of Leo Zucker

(57) ABSTRACT

A facet joint is exposed at one side of the spine during surgery. An inclinometer is mounted on an elongated probe, and a pin is fixed on a spinous process near the exposed joint. The probe is swivelled about the pin so that a distal end of the probe contacts the joint and the inclinometer indicates a corresponding first trajectory. A second trajectory from the pin to an unexposed facet joint on the opposite side of the spine is defined as being symmetrical with the first trajectory about the spine axis. The inclinometer is mounted on a guide sleeve, and the sleeve is swivelled about the pin into the second trajectory. A wire is inserted through the sleeve until a tip of the wire penetrates the unexposed joint percutaneously. A facet screw is advanced over the wire and threaded percutaneously into the unexposed facet joint after the sleeve is withdrawn.

4 Claims, 10 Drawing Sheets

(56) References Cited

U.S. PATENT DOCUMENTS

| | | |
|---|---|---|
| 2007/0055291 A1* | 3/2007 | Birkmeyer et al. .......... 606/130 |
| 2007/0083218 A1* | 4/2007 | A. Morris ..................... 606/157 |
| 2007/0270877 A1 | 11/2007 | Park |
| 2008/0255619 A1 | 10/2008 | Schneiderman et al. |
| 2008/0269757 A1 | 10/2008 | McMinn |
| 2008/0300605 A1 | 12/2008 | Rinner |
| 2009/0287255 A1* | 11/2009 | Erickson et al. ............. 606/279 |
| 2010/0023018 A1 | 1/2010 | Theofilos |
| 2010/0036384 A1 | 2/2010 | Gorek et al. |
| 2010/0087823 A1 | 4/2010 | Kondrashov |
| 2010/0222815 A1 | 9/2010 | Simonson |

\* cited by examiner

IMPLANTING FACET JOINT SCREWS PERCUTANEOUSLY

CROSS REFERENCE TO RELATED APPLICATION

The present application claims priority under 35 U.S.C. §119(e) of U.S. Provisional Patent Application No. 61/389,906 filed Oct. 5, 2010, which is incorporated by reference in its entirety.

BACKGROUND OF THE INVENTION

Field of the Invention

The present invention relates generally to spinal implant procedures and tools, and particularly to a procedure and tools for implanting facet joint screws percutaneously.

Discussion of the Known Art

U.S. Pat. No. 7,717,919 discloses a mechanical alignment jig (see FIGS. 17-20) for aligning the axis of an external cannula guide block to coincide with, or run parallel to, a determined internal target path along which a screw is to be delivered percutaneously to either one of two facet joints at a given level of a patient's spine. Each internal guide path is initially determined by a surgeon using conventional imaging means and by inserting markers.

Further, U.S. Patent Application Pub. No. 2010/0023018 describes a bilateral drilling guide (see FIG. 1) that is fixed by a clamp on the spinous process of a vertebral body in a patient's spine. An extension is mounted to extend laterally from the spinous process, and to rotate 180 degrees between either side of the vertebral body. A pointing device, a protractor, and a drill bushing are mounted on the extension to enable a number of drilling axes to be defined toward the body.

U.S. Pat. No. 4,907,577 discloses a transpedicle drill jig having a pair of drill guiding sleeves (see FIGS. 3-6) the distal ends of which can be placed at desired positions on either side of a vertebral body of a patient's spine. In use, the jig is held against but is not fixed to the vertebral body.

New products for facet fixation have been offered to complement the use of unilateral pedicle screws or stand-alone cages in spinal surgery. Many of these products do not fixate rigidly, and/or they are cumbersome to implant properly. Problems have been encountered mainly in the process of targeting and placing the screws in the patient's spine, rather than in fixation where conventional facet screws have proven to achieve the best results.

To achieve a minimally invasive spinal fusion procedure, surgeons may implant pedicle screws unilaterally by exposing the spine only at the side in which the screws are to be inserted, and provide contralateral facet joint fixation by use of facet screws inserted percutaneously with the aid of X-ray imaging and/or other navigation equipment. Notwithstanding the known art, there is a need for tool or system that will enable a surgeon to determine a first drilling axis along which a facet screw can be inserted percutaneously and accurately into a given side of a patient's spine, based only on the geometry of a second drilling axis determined at the opposite side of the spine, and without a need for X-ray or other navigation techniques. Such a tool could substantially reduce the time required to implant facet screws or other devices percutaneously at the given side of the spine.

SUMMARY OF THE INVENTION

According to the invention, a surgical tool system for implanting facet joint screws percutaneously in a patient's spine, includes an elongated probe, and an inclinometer arranged and configured to mount on the probe for sensing angular deviations of the probe from a horizontal and a vertical plane, and for indicating corresponding trajectories of the probe. A guide anchor screw or pin is configured to be fixed on a spinous process on a given spinal vertebra, and the pin has a guide opening or channel for passage of the probe, and for enabling the probe to swivel so that a distal end of the probe contacts an exposed first facet joint on one side of the spine and the inclinometer indicates a first trajectory from the pin to the first facet joint. The system also includes a guide sleeve on which the inclinometer is mounted, and the pin on the spinous process enables the sleeve to swivel about the pin to a position at which the inclinometer indicates a second trajectory from the pin to an unexposed second facet joint on the opposite side of the spine, such that the second trajectory is symmetrical with the first trajectory about the spine axis. A guide wire is dimensioned to be inserted through the guide sleeve so that a distal tip of the wire penetrates the second facet joint percutaneously. A cannulated facet screw is arranged to be advanced over the guide wire after the sleeve is withdrawn, and the screw is threaded percutaneously through the second facet joint.

According to another aspect of the invention, a method of implanting facet joint screws percutaneously in a patient's spine includes exposing a first facet joint at one side of the spine while performing a surgical procedure, providing an elongated probe, and mounting an inclinometer on the probe to indicate angular trajectories of the probe. A guide anchor screw or pin is fixed on a vertebral spinous process in the vicinity of the first facet joint, and the probe is swivelled about the pin so that a distal end of the probe contacts the exposed first facet joint and the inclinometer indicates a corresponding first trajectory from the pin to the first facet joint. A second trajectory from the pin to an unexposed second facet joint on the opposite side of the spine is defined as being symmetrical with the first trajectory about the spine axis. The inclinometer is mounted on a guide sleeve, and the sleeve is swivelled about the pin on the spinous process to a position at which the inclinometer indicates the second trajectory. A guide wire is inserted through the sleeve until a distal tip of the wire penetrates the second facet joint percutaneously. After the sleeve is withdrawn, a facet screw is advanced over the guide wire and threaded percutaneously into the second facet joint.

For a better understanding of the invention, reference is made to the following description taken in conjunction with the accompanying drawing and the appended claims.

DETAILED DESCRIPTION OF THE INVENTION

The present invention relates to a tool or system for locating and placing facet screws or other implants in a surgical patient's spine, typically for the purpose of obtaining a spinal fusion. The inventive system allows certain implants to be placed percutaneously with accuracy and in minimal time.

Figure 1:
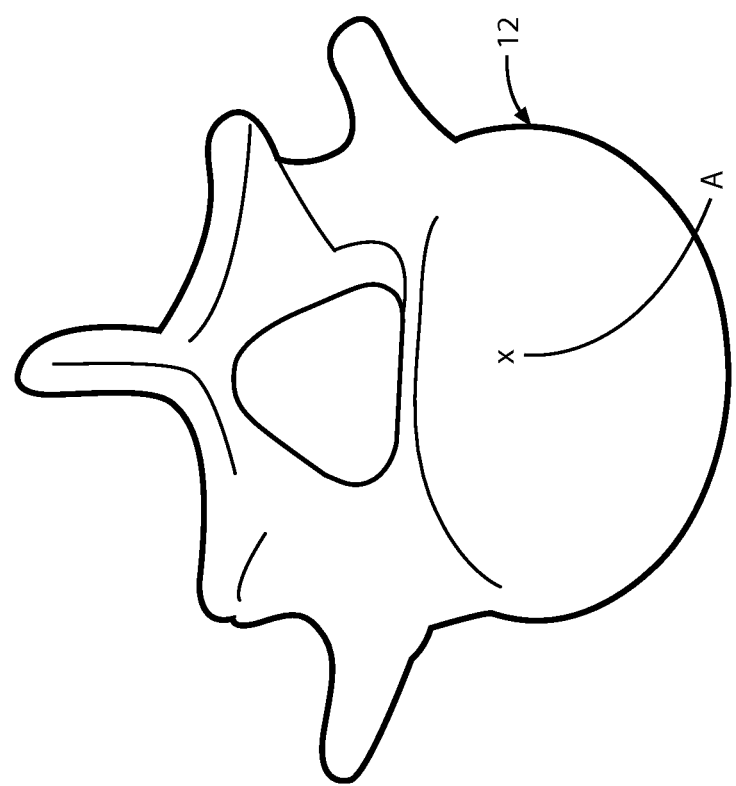
FIG. 1 shows a spinal vertebra as viewed in a plane perpendicular the axis of a human spine.
Figure 2B:
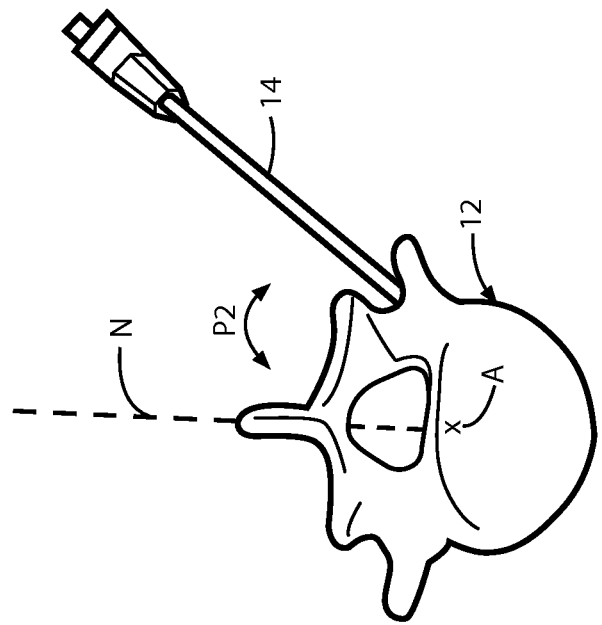
FIGS. 2(a) and 2(b) are views of the vertebra as in FIG. 1, and including a probe to demonstrate a reflective symmetry of the spine, according to the invention.
Figure 2A:
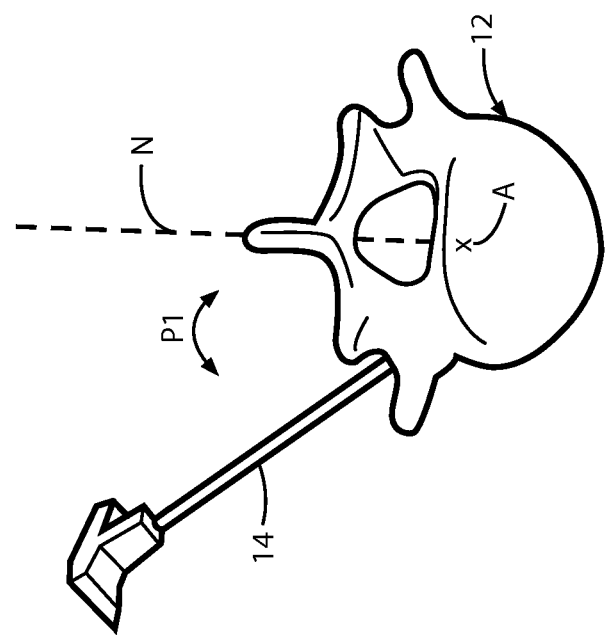

It has been discovered and observed that except for cases of scoliosis, congenital deformity or tumor, the vertebral bones of a normal human spine have what is referred to herein as "reflective symmetry". See, for example, vertebra 12 in FIG. 1. Specifically, when the vertebra 12 is viewed in a plane perpendicular to spine axis A as in FIGS. 1, 2(a) & 2(b), the body of the vertebra 12 on the left side of a normal line N drawn perpendicular to the spine axis A, is a mirror image physically of the body of the vertebra 12 on the right side of the line N. Accordingly, if a probe 14 is used to form an entry point on the left pedicle of the vertebra 12 as viewed in FIG. 2(a) and the probe 14 defines an angle P1 with line N, the probe 14 will define an angle P2 equal to P1 in magnitude with respect to line N when forming a corresponding entry point on the right pedicle of the vertebra 12 as viewed in FIG. 2(b).

Figure 3A:
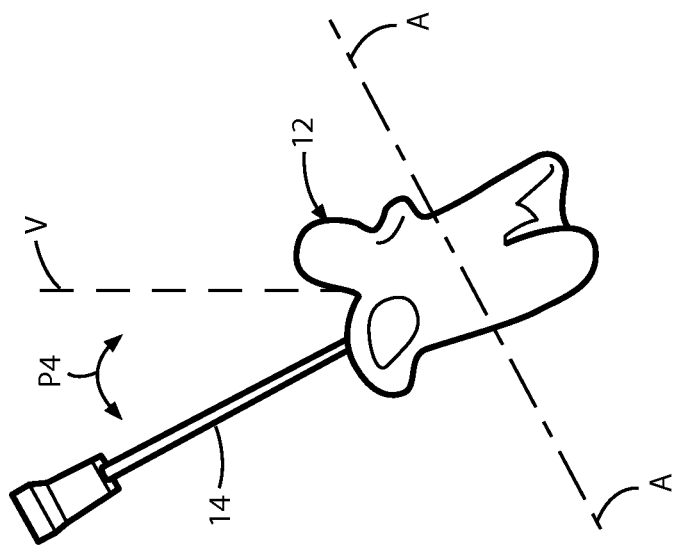
FIGS. 3(a) and 3(b) show the vertebra of FIG. 1, showing opposite side end portions of the vertebra and the probe to demonstrate reflective symmetry according to the invention.
Figure 3B:
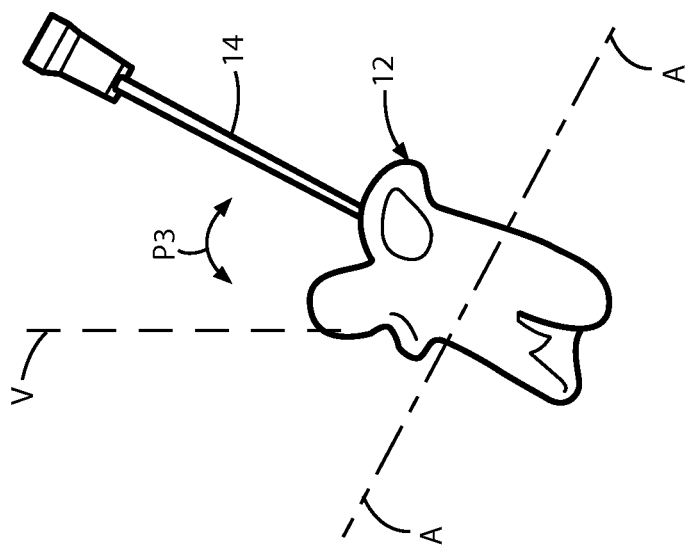

Further, when the lateral side ends of the vertebra 12 are viewed in planes parallel to the spine axis A as in FIGS. 3(a) & 3(b), the side end portions of the vertebra 12 are also mirror images of one another in three-dimensional space. That is, if the probe 14 as it is viewed in FIG. 3(a) defines an angle P3 with a vertical line V, the probe 14 will define an angle P4 equal to P3 in magnitude with respect to line V as the probe 14 is viewed in FIG. 3(b). The inventive system uses to advantage the reflective symmetry of the spine to allow a facet screw or other fixation device to be implanted in the vertebra 12 percutaneously and accurately along a first drilling axis in one side of the vertebra, according to the geometry of a second drilling axis that is determined while the opposite side of the vertebra is exposed during a spinal fusion procedure.

EXAMPLE

Posterior Unilateral Approach

Figure 5:
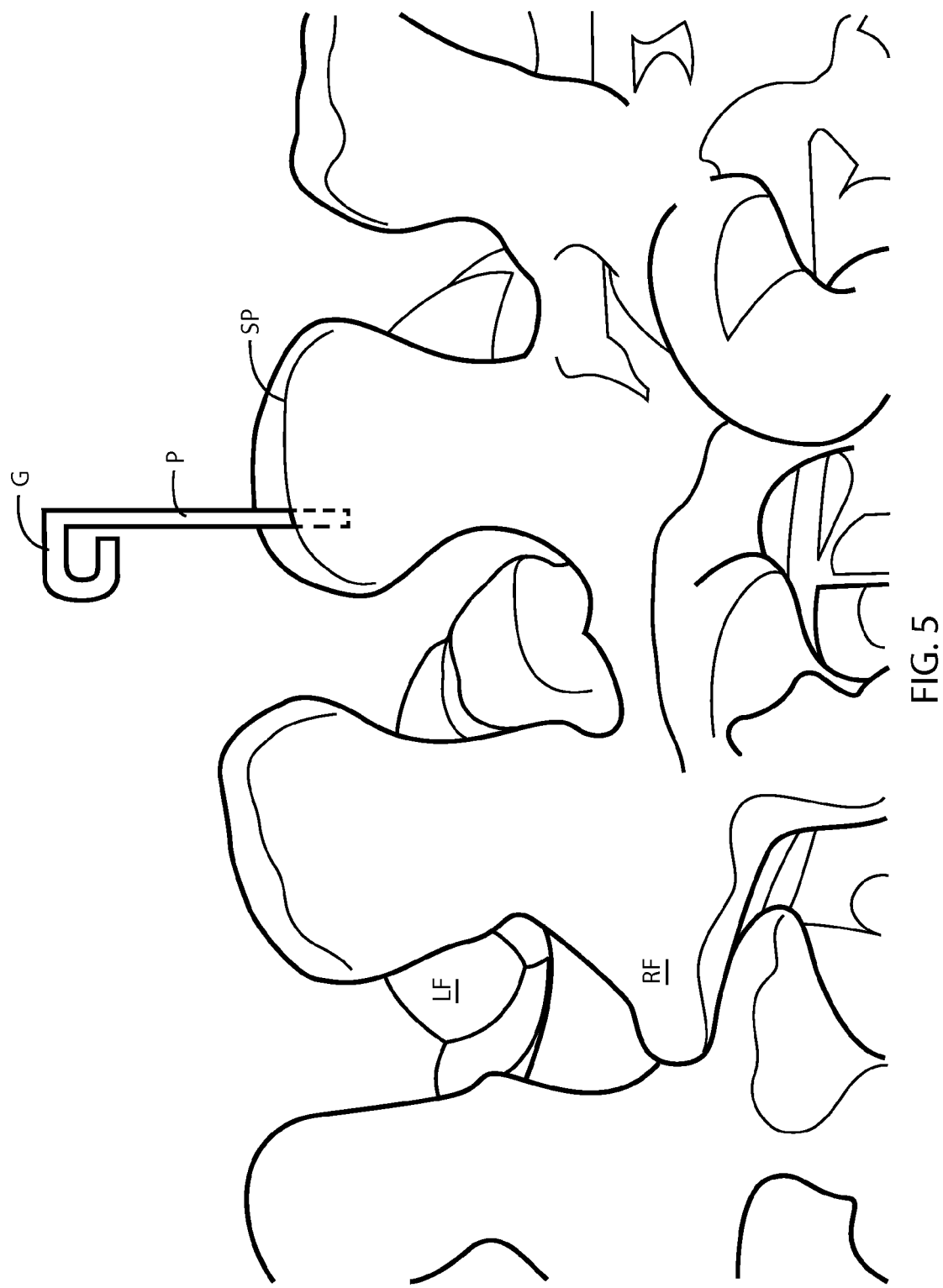
FIG. 5 shows the lumbar portion of the spine, and a guide anchor screw or pin inserted in the top edge of a spinous process according to the invention.
Figure 6:
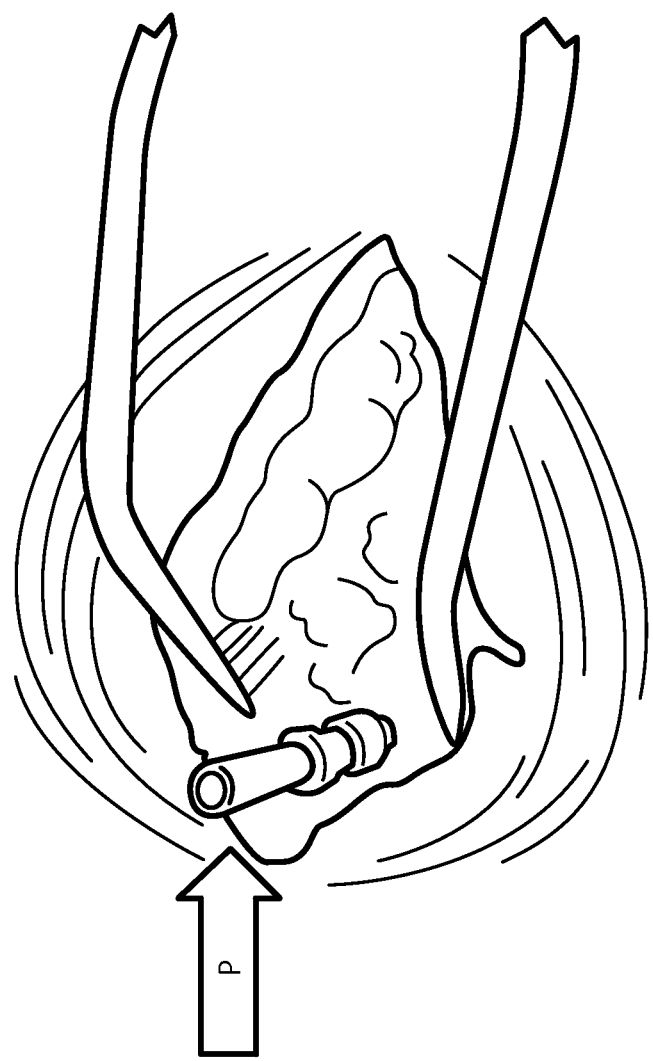
FIG. 6 shows an incision in the patient's back exposing one side of the spine and the anchor pin inserted in the spinous process.

A hybrid construct for a L4-L5 fusion is desired using unilaterally placed pedicle screws and contralateral facet fixation. An incision is made in preparation for placement of the pedicle screws at the side of the patient's spine corresponding to the patient's right side, which is toward the left as viewed in FIG. 4. Before exposing and removing the facet joint RF in FIG. 4 in order to accommodate the construct, a tool guide anchor screw or pin P according to the invention is inserted in the L3 spinous process SP so that the head of the pin P protrudes vertically above the top edge of the spinous process, and above the incision as depicted in FIGS. 5 and 6. A gap opening G is formed at the head of the guide pin P for supporting a probe that passes through the opening G (see FIGS. 7 & 8), and for allowing the probe to swivel on the head of the pin so that the distal end of the probe can swing toward the exposed right facet joint RF.

Figure 4:
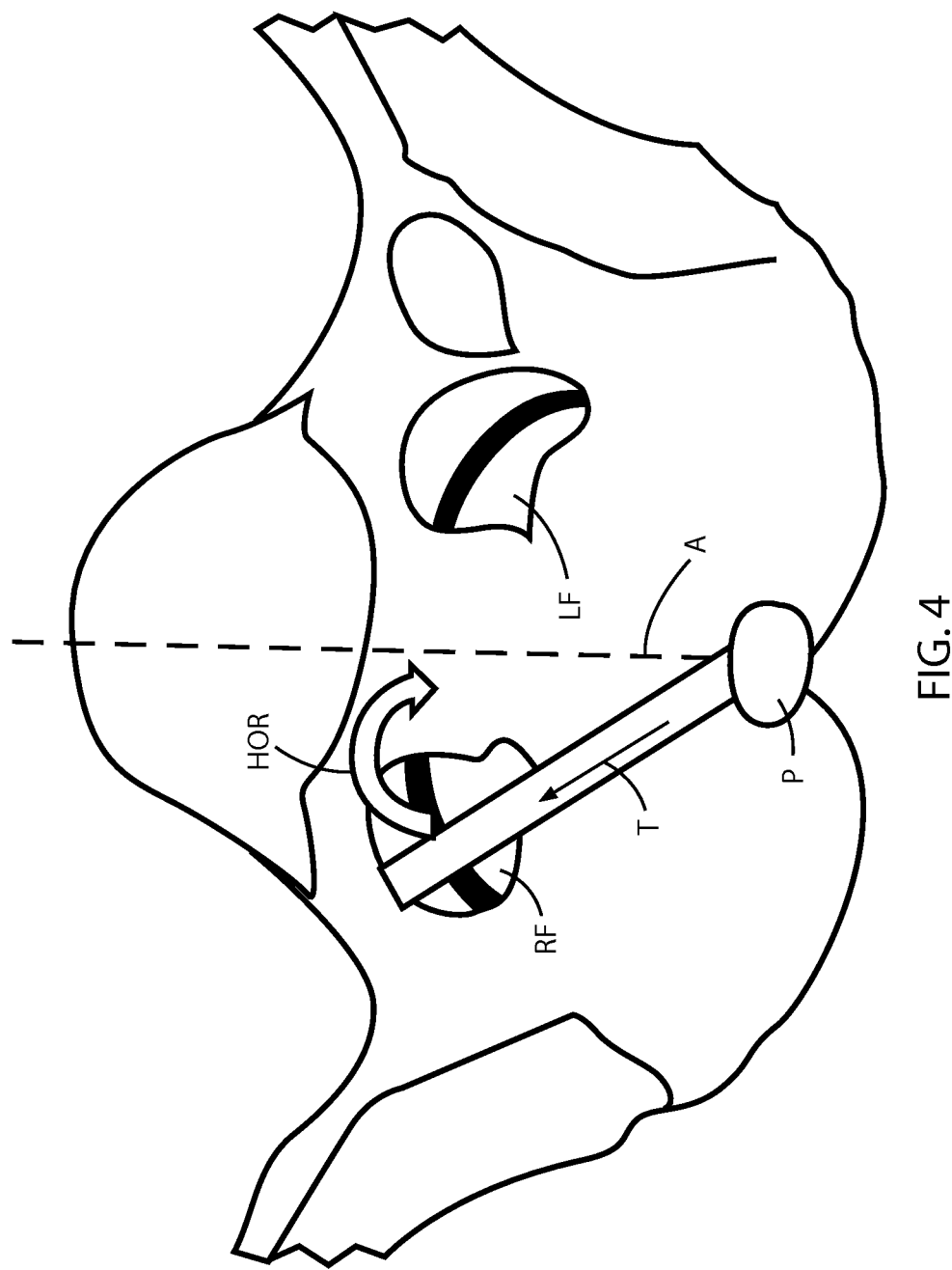
FIG. 4 is a cross sectional image of a lumbar portion of a patient's spine in a plane transverse the axis of the spine, and showing two facet joints on either side of the spine axis.
Figure 7:
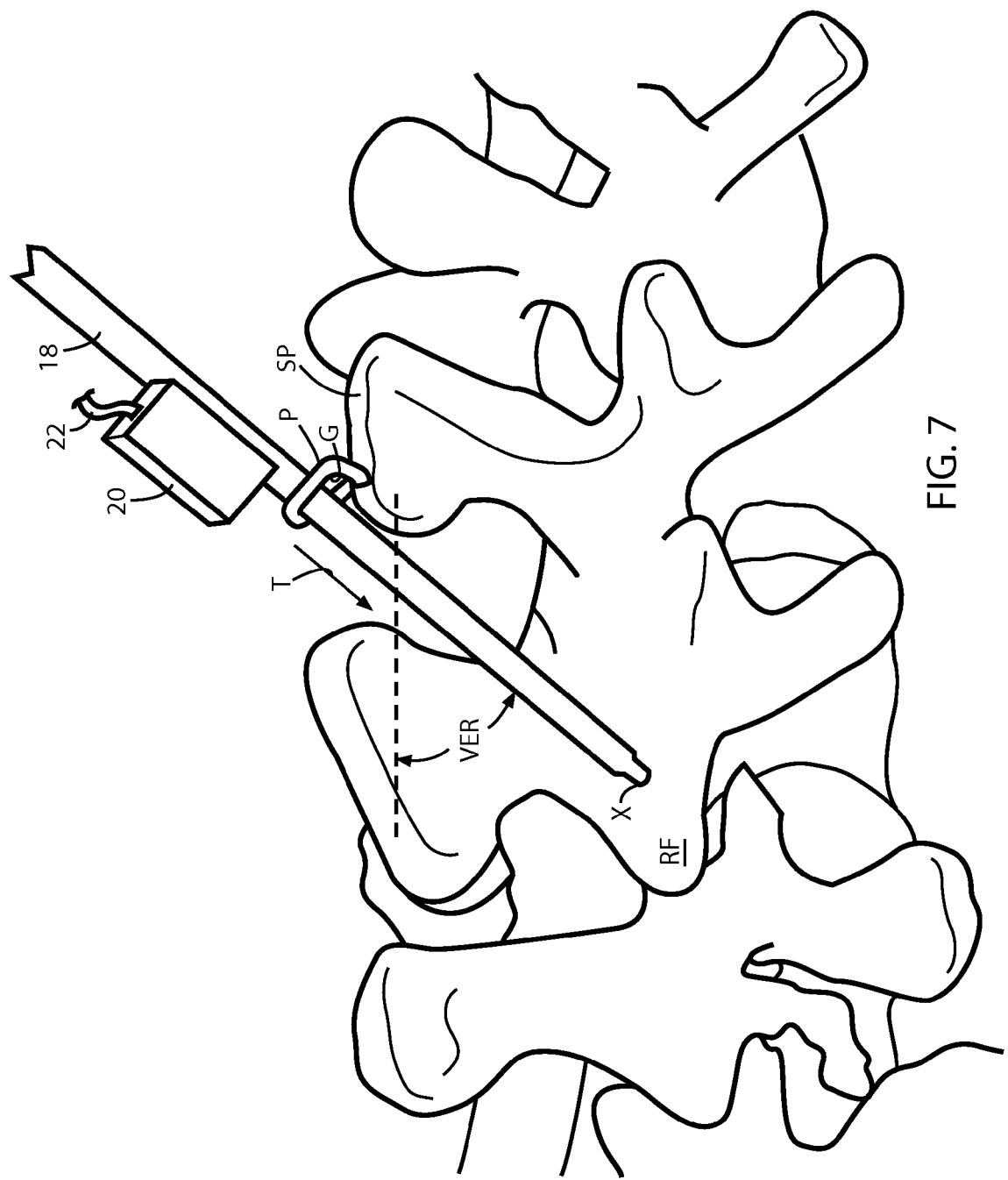
FIG. 7 shows a probe passing through a gap in the anchor pin and defining a first trajectory toward a facet joint on one side of the spine.

As illustrated in FIGS. 4 and 7, a trajectory T is determined for the probe D when passing through the opening G at the head of the anchor pin P, and a position X on the right facet joint RF at which a facet screw would be inserted in the event a fixation of the joint RF were to be performed. The trajectory T may be defined by use of a conventional inclinometer, for example, a model H4PD1-22 inclinometer available from Rieker™ which provides dual axis inclination sensing using an element referenced to gravity over a wide temperature range. Inclinometers have been incorporated in devices or probes for determining a trajectory for placement of pedicle screws. See, e.g., U.S. Patent Application Pub. No. 2010/0087823 (Apr. 8, 2010) and Pub. No. 2010/0036384 (Feb. 11, 2010), both of which are incorporated by reference.

As shown in FIG. 7, a probe 18 with an associated inclinometer 20 operatively fixed on the outside circumference of the probe, passes through the opening G formed at the top of the anchor pin P inserted in spinous process SP. The distal tip of the probe 18 is visibly positioned by the surgeon at a point X on the facet joint RF where a facet screw would be inserted if a fixation of facet joint RF were to be performed.

The trajectory T of the probe 18 from the head of the anchor pin P to the insertion point X on the facet joint RF is then defined by the inclinometer 20 with respect to the head of the anchor pin P by, e.g., (a) degrees HOR relative to the spine axis A in a horizontal plane, as shown in FIG. 4, and (b) degrees VER downward relative to the spine axis A in a vertical plane, as shown in FIG. 7. Signals corresponding to both of the angular measurements HOR and VER are transmitted from the inclinometer 20 over an associated cable 22, or wirelessly, and are processed in a known manner to determine the magnitudes of the angles.

Both of the angles HOR and VER are stored and/or displayed for later reference. The right facet joint RF is then removed, and pedicle screws and rods are placed by the surgeon in the L4-L5 level at the exposed side of the patient's spine. Prior to removing the facet joint RF, the surgeon can determine the length of a facet screw need to fix the left facet joint LF on the opposite side of the spine, by measuring the exposed right facet joint RF.

Figure 8:
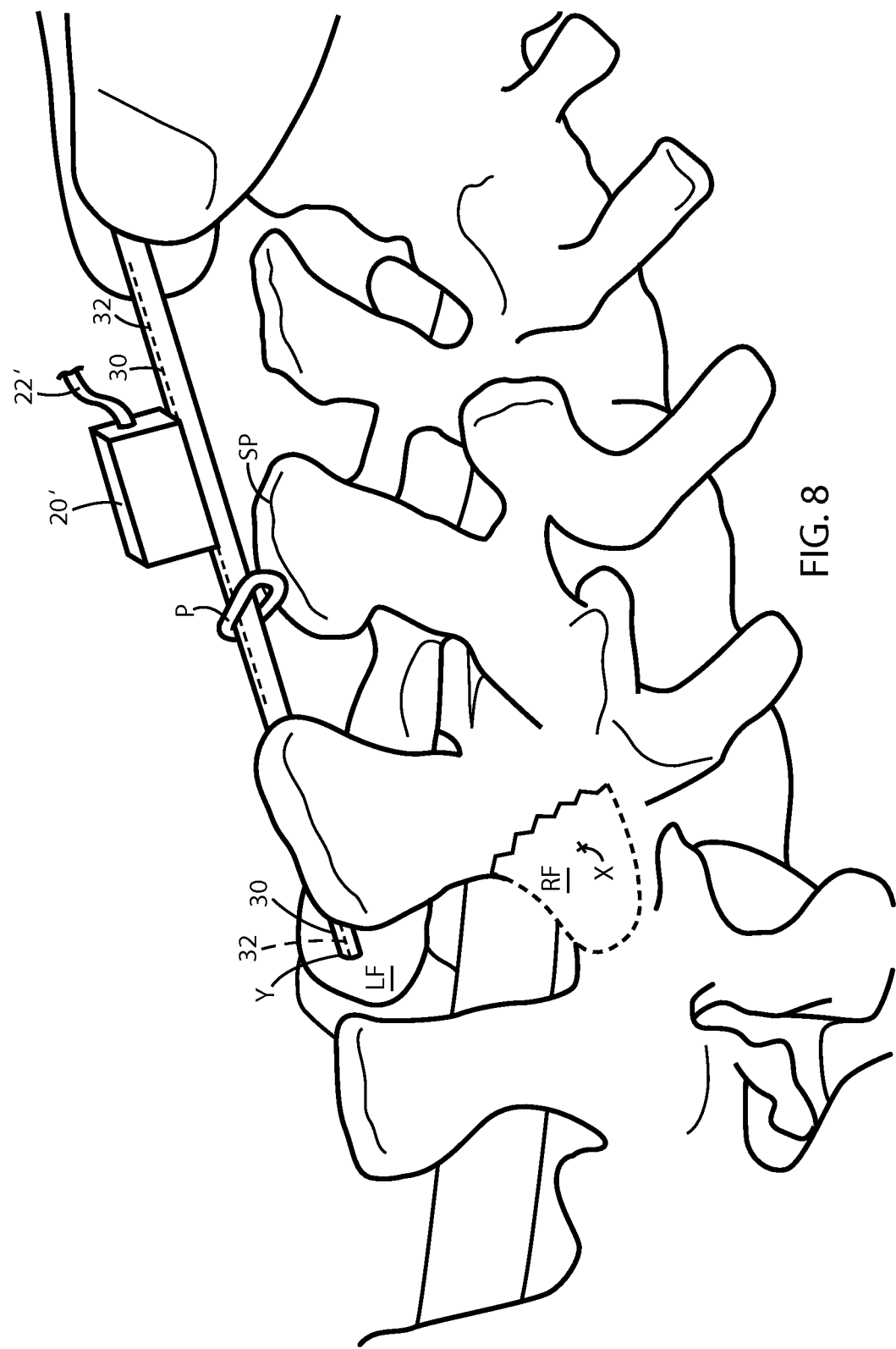
FIG. 8 shows the probe in FIG. 7 defining a second trajectory toward a facet joint on the other side of the spine and at the same level as in FIG. 7.
Figure 11:
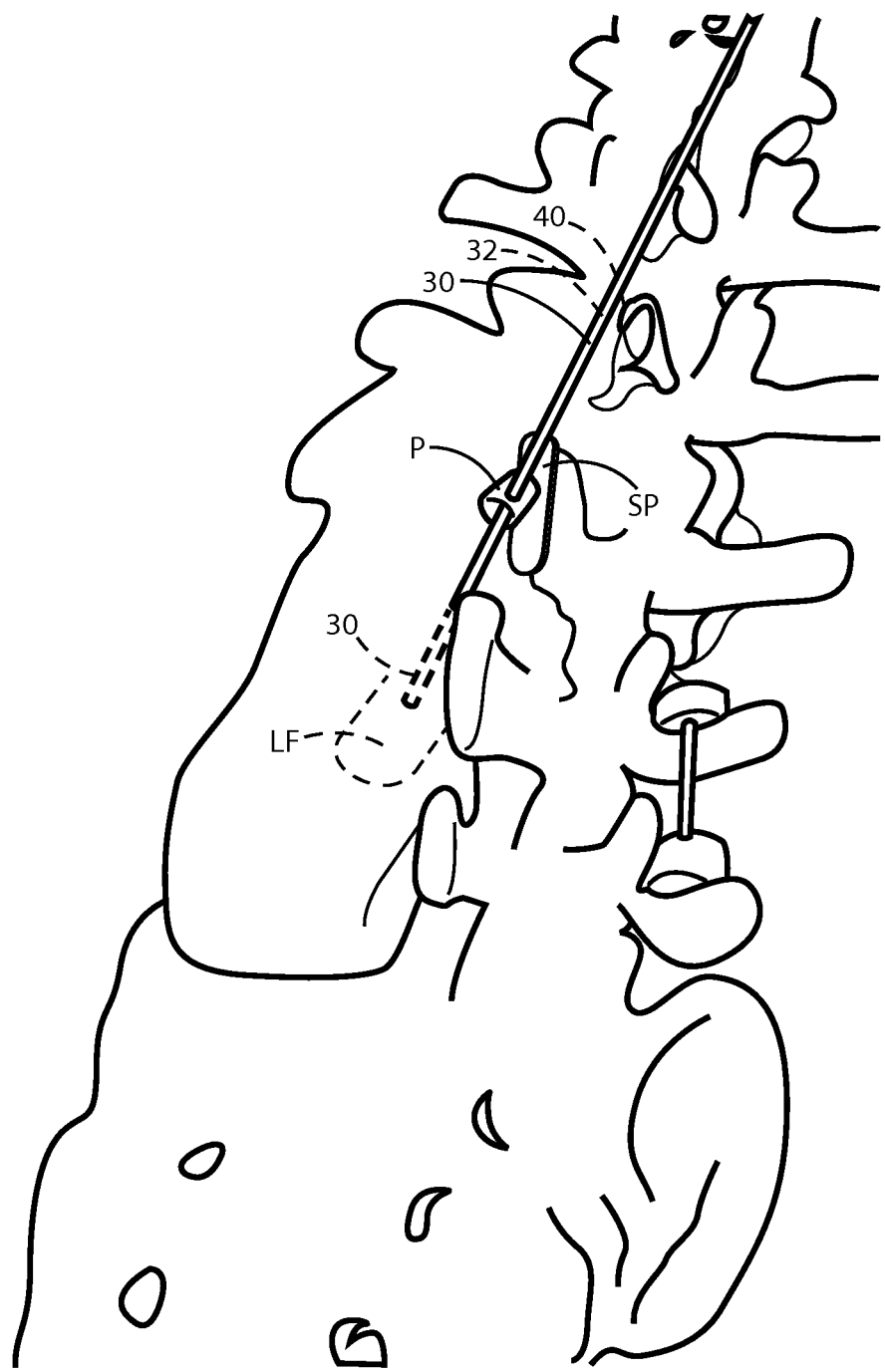
FIG. 11 shows a guide or K-wire passing through a gap in the anchor pin of FIG. 9, while being inserted percutaneously into a facet joint at an unexposed side of the spine.

Without making another incision or opening to expose the other side of the patient's spine, a contralateral facet screw is placed percutaneously and rapidly according to the angular measurements HOR and VER as obtained above. As shown in FIG. 8, a drill bit guide sleeve 30 has the same or an equivalent inclinometer 20' fixed along its outer circumference and aligned in the same orientation with respect to the sleeve as the inclinometer 20 on the probe 18. The inner diameter of the sleeve 30 should be sufficient to allow passage of a drill bit, and an inner, second guide sleeve 32 may be routed concentrically inside the outer sleeve 30 and have an inner diameter dimensioned for passage of a conventional surgical drill bit guide wire or "K-wire". The sleeve 30 with the inner sleeve contained 32 inside, is passed through the opening G in the anchor pin P atop the spinous process SP as shown in FIG. 8. The surgeon swivels the sleeve 30 over the unexposed side of the spine in a horizontal plane by HOR degrees, that is, by the same number of degrees the probe 18 was swung horizontally over the exposed side of the spine when determining the trajectory for placing a screw in the facet joint RF (now removed). The surgeon swivels the sleeve 30 downward in a vertical plane by VER degrees, that is, by the same number of degrees the probe 18 was swung downward to determine the proper trajectory for screw placement in facet joint RF. The sleeve 30 is advanced percutaneously into contact with the left facet joint LF (see FIG. 11). Thus, the sleeve 30 defines a correct trajectory for inserting a screw in the left facet joint LF, based on the geometry of the trajectory determined for the right facet joint RF on the opposite side of the patient's spine.

A drill bit guide wire or "K-wire" 40 is inserted in the proximal end of the inner guide sleeve 32 contained in the outer sleeve 30, and the wire is advanced percutaneously toward the unexposed side of the patient's spine until the tip of the wire contacts the left facet joint LF. See FIG. 11. The proximal end of the wire may be fastened to a drill, and the tip of the wire drilled or manually urged to a certain depth into the joint LF. The inner guide sleeve 32 is withdrawn from the outer sleeve 30 and the guide wire 40, and a conventional cannulated drill bit is slid over the guide wire and through the sleeve 30. The drill bit is advanced percutaneously into contact with the facet joint LF, and then driven a sufficient distance through the joint LF as to allow a conventional facet screw to be threaded through the joint for fixation.

The drill bit and the outer sleeve 30 are then withdrawn from the guide wire 40, and a cannulated facet screw is passed over the guide wire. To facilitate passage of the facet screw over the guide wire, the wire may be brought outside of the gap opening G, for example, by urging the wire sideways through a narrow slot formed at the periphery of the opening G and away from the anchor pin P. The facet screw is advanced percutaneously on the guide wire toward the facet joint LF, and is driven by a cannulated drive bit through the opening formed in the joint LF by the drill bit. The drive bit and the guide wire are then withdrawn from the joint LF, and the anchor pin P is removed from the spinous process SP.

Figure 12:
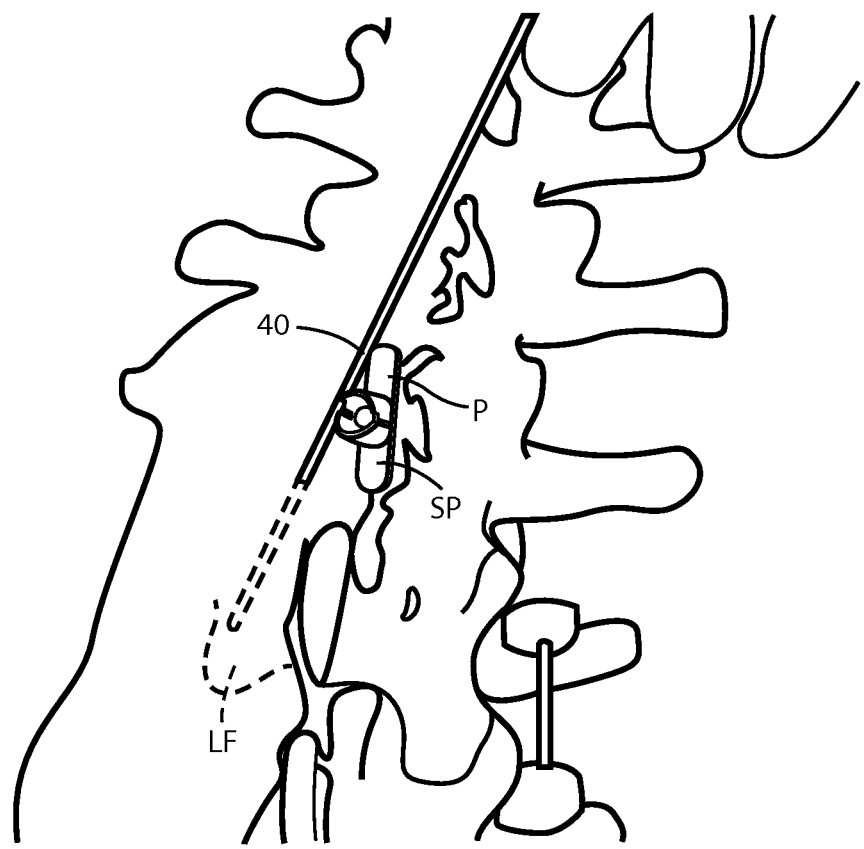
FIG. 12 shows the guide wire in FIG. 11 removed from the anchor pin prior to guiding a cannulated facet screw to the facet joint for insertion.
Figure 9:
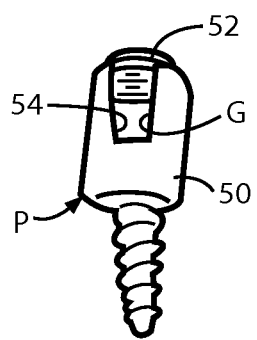
FIG. 9 shows another embodiment of the guide anchor pin.
Figure 10:
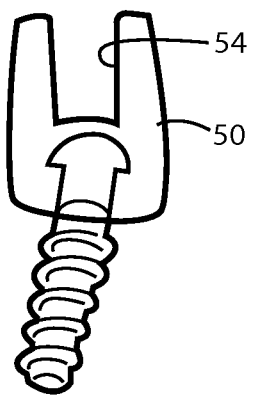
FIG. 10 shows the anchor pin in FIG. 9 with a cap removed.

FIGS. 9 and 10 show a preferred embodiment of the anchor pin P in the form of a polyaxial surgical screw including a swivel head 50 and a threaded cap 52. Gap opening G is bounded by an open channel 54 formed across the top of the swivel head 50 and the cap 52 threaded onto the head 50. As shown in FIG. 12, once the distal end of the guide wire 40 is fixed in the facet joint LF, the guide wire may be removed from within the gap opening G in the anchor pin P by unscrewing the threaded cap 52 from the swivel head 50 as in FIG. 10. With the guide wire removed from the anchor pin P, neither the cannulated facet screw nor the drill bit would need to be able to pass through the gap opening G formed in the pin P.

It is contemplated that a surgical tool system kit for placement of facet joint screws according to the invention may be provided to include, for example:

(a) an elongated probe;
(b) an inclinometer configured to mount on the probe in such a position as to sense an angular deviation of the probe from a horizontal and a vertical plane, and to output corresponding signals for processing;
(c) a guide anchor screw or pin with a polyaxial swivel head and a guide opening or channel formed in or on the head;
(d) a length of guide wire or K-wire;
(e) a drill bit guide sleeve with a removable concentric inner sleeve;
(f) a cannulated drill bit; and
(g) cannulated facet screws of one or more different lengths.

The inventive tool system may also be adapted to place a screw or an implant into other parts of the spine such as, e.g., a pedicle, transverse process, lamina, etc, as long as the targeted anatomic structures have reflective symmetry with the corresponding structures on the opposite side of the spine. Moreover, facet screws or other implants may still be placed percutaneously at one side of the spine in a traditional manner based on X-ray and/or other imaging techniques, and the inventive tool system can then be used to place implants percutaneously at the other side of the spine in significantly less time.

While the foregoing represents preferred embodiments of the invention, it will be understood by those skilled in the art that various modifications and changes may be made without departing from the spirit and scope of the invention, and that the invention includes all such modifications and changes as are within the bounds of the following claims.

I claim:

1. A surgical tool system for implanting facet joint screws percutaneously, comprising:
    an elongated probe;
    an elongated guide sleeve;
    an inclinometer constructed and arranged for mounting on the probe and sensing angular deviations of the probe from a horizontal and a vertical plane, and for indicating corresponding trajectories of the probe;
    a guide anchor screw or pin configured to be fixed on a spinous process on a given vertebra of a patient's spine, and the screw or pin has a guide opening or channel dimensioned for passage of the probe, and for enabling the probe to swivel so that a distal end of the probe contacts an exposed first facet joint on one side of the spine, and the inclinometer when mounted on the probe indicates a first trajectory from the screw or pin to the first facet joint;
    the guide sleeve is constructed and arranged so that the inclinometer or other like inclinometer is mountable on the sleeve, and the guide opening or channel in the screw or pin when fixed on the spinous process enables the guide sleeve to swivel about the screw or pin to a position at which the inclinometer indicates a second trajectory from the screw or pin to an unexposed second facet joint on the opposite side of the spine, wherein the second trajectory and the first trajectory are symmetrical with respect to an axis of the spine;
    a length of guide wire dimensioned for passing through the guide sleeve along the second trajectory so that a distal tip of the guide wire penetrates the second facet joint percutaneously; and
    a cannulated facet screw formed and dimensioned to slide over the guide wire for threading into the second facet joint percutaneously after the guide sleeve is withdrawn;
    wherein the guide anchor screw or pin is in the form of a polyaxial surgical screw or pin including a swivel head and a cap.

2. A surgical tool system according to claim 1, including a drill bit constructed and arranged for advancing over the guide wire and for driving through the second facet joint percutaneously.

3. A method of implanting facet joint screws percutaneously in a patient's spine, comprising:
  exposing a first facet joint on one side of a patient's spine when performing a surgical procedure at a given level of the spine;
  providing an elongated probe, and an inclinometer configured to mount on the probe for sensing angular deviations of the probe from a horizontal and a vertical plane, and for indicating corresponding trajectories of the probe;
  fixing a guide anchor screw or pin on a vertebral spinous process in the vicinity of the first facet joint;
  swivelling the probe about the screw or pin so that the inclinometer indicates a first trajectory from the screw or pin to the first facet joint exposed at the one side of the spine;
  determining a second trajectory from the screw or pin to an unexposed second facet joint on the opposite side of the spine whereby the second trajectory is symmetrical with the first trajectory about an axis of the spine;
  mounting the inclinometer or a like inclinometer on an elongated guide sleeve;
  swivelling the guide sleeve about the anchor screw or pin on the spinous process until the inclinometer mounted on the guide sleeve indicates the guide sleeve is at the second trajectory;
  inserting a guide wire through the guide sleeve at the second trajectory, and penetrating the second facet joint percutaneously with a distal tip of the guide wire;
  advancing a facet screw over the guide wire and threading the facet screw into the second facet joint percutaneously after the guide sleeve is withdrawn; and
  providing the guide anchor screw or pin in the form of a polyaxial surgical screw or pin comprising a swivel head and a cap.

4. A method of implanting facet joint screws according to claim 3, including, prior to advancing a facet screw over the guide wire, advancing a drill bit over the wire, and driving the drill bit through the second facet joint percutaneously.

* * * * *